(12) United States Patent
Wilson

(10) Patent No.: US 9,886,592 B2
(45) Date of Patent: Feb. 6, 2018

(54) MEDICAL ALERT COMPUTER INTERFACE TAMPER-PROOF SECURE DEVICE

(76) Inventor: Geraldine Wilson, Milford, CT (US)

( * ) Notice: Subject to any disclaimer, the term of this patent is extended or adjusted under 35 U.S.C. 154(b) by 1728 days.

(21) Appl. No.: 12/841,490

(22) Filed: Jul. 22, 2010

(65) Prior Publication Data

US 2012/0023592 A1    Jan. 26, 2012

(51) Int. Cl.
| | |
|---|---|
| H04L 29/00 | (2006.01) |
| G06F 21/62 | (2013.01) |
| G06F 19/00 | (2011.01) |
| G06F 21/33 | (2013.01) |
| G06Q 50/22 | (2012.01) |
| G06Q 50/24 | (2012.01) |
| H04L 29/06 | (2006.01) |

(52) U.S. Cl.
CPC ........ *G06F 21/6245* (2013.01); *G06F 19/323* (2013.01); *G06F 21/335* (2013.01); *G06Q 50/22* (2013.01); *G06Q 50/24* (2013.01); *H04L 63/08* (2013.01); *G06F 2221/2141* (2013.01)

(58) Field of Classification Search
USPC ....... 713/155, 161, 168, 170, 182, 185, 193; 726/2–5, 9, 17, 20, 21, 27–30
See application file for complete search history.

(56) References Cited

U.S. PATENT DOCUMENTS

| 6,768,452 | B2 | 7/2004 | Gilkes | |
|---|---|---|---|---|
| 7,003,495 | B1* | 2/2006 | Burger et al. | 705/50 |
| 7,251,470 | B2 | 7/2007 | Faucher | |
| 7,448,905 | B1 | 11/2008 | Lin | |
| 7,596,703 | B2* | 9/2009 | Kohiyama et al. | 713/193 |
| 2004/0128518 | A1 | 7/2004 | Cavers | |
| 2005/0107673 | A1 | 5/2005 | Ball | |
| 2006/0015368 | A1 | 1/2006 | Hockey | |
| 2008/0016738 | A1 | 1/2008 | Talbott | |
| 2008/0027752 | A1 | 1/2008 | Phan | |
| 2008/0319798 | A1* | 12/2008 | Kelley | 705/3 |
| 2009/0295569 | A1 | 12/2009 | Corwin | |
| 2010/0023528 | A1 | 1/2010 | Cion | |
| 2010/0033320 | A1 | 2/2010 | Dougherty-Clark | |
| 2010/0102123 | A1 | 4/2010 | Skowronek | |

* cited by examiner

*Primary Examiner* — Joseph P Hirl
*Assistant Examiner* — Leynna Truvan
(74) *Attorney, Agent, or Firm* — Symbus Law Group, LLC; Clifford D. Hyra

(57) ABSTRACT

A medical information system includes a portable device and remote authentication computing device. The portable device stores a person's personal medical information, which it does not allow to be accessed without authentication, and has an activation mechanism and a computing device communication mechanism. The remote authenticating computing device is connected to a computing device network and stores authentication information and has an authentication software module and a diagnostic software module. The activation mechanism communicates the device with the remote authenticating computing device. The authentication software module requests authentication information from a user, receives input authentication information, verifies received authentication data against the stored authentication information, and after successful verification allows the medical information to be accessed by a computing device. The diagnostic software module determines whether the portable device has been damaged or tampered with and if so the stored medical information is destroyed.

29 Claims, 2 Drawing Sheets

MEDICAL ALERT COMPUTER INTERFACE TAMPER-PROOF SECURE DEVICE

BACKGROUND

The present invention relates to the fields of secure electronic devices and medical alert devices.

Existing medical alert bracelets are metal and engraved with important medical information such as an allergy, in case the wearer is incapacitated and unable to communicate this information to medical professionals. They are not able to store or communicate large amounts of information or to secure information against unauthorized viewing.

Needs exist for improved medical alert devices.

SUMMARY

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description. Rather, the scope of the invention is defined by the appended claims.

In certain embodiments, the disclosed embodiments may include one or more of the features described herein.

As used herein, non-transitory computer-readable media comprise all computer-readable media, with the sole exception being a transitory, propagating signal.

An ibutton is a small hardware, embedded data system containing a computer chip and is capable of storing applications and data in a durable case with a unique and unalterable factory-assigned identifier/key. ibuttons are embedded software devices that have power sources (and th s an end of life) and enough memory to accommodate a secure application. Ibuttons are chosen o accommodate the size of the application that is needed. ibuttons can be read and written to with the 1-wire protocol, in which a single contact is used for power and data transfer, and a second contact for ground. 1-wire USB adapters allow ibuttons to be accessed with a standard computer USB port. Various types of ibuttons are available for different applications, including secure ibuttons with password protected memory and challenge response algorithms. However, the invention is not limited to the ibutton embodiment. Other portable memory may be envisioned as well.

The configuration of computing devices described herein may be implemented in software, hardware, or a combination thereof. For example, in some embodiments the portable device and authenticating server are configured using various software modules programmed on one or more non-transitory computer readable media, where for example each step of a process is carried out by a different software module.

A new medical alert device stores an individual's medical information in a computer readable medium and has a wired or wireless connection device for communicating with a computing device. The device protects the information against unauthorized access, and has a wearable casing such that the device can be worn for example as an item of jewelry similar to med alert bracelets currently in use. This combination of elements may be referred to as a Patient Medical Data Storage Tag, or PMDST for short.

In one embodiment, a USB drive is connected with an ibutton in a medic alert bracelet/dog tag necklace/wearable jewelry. The ibutton authenticates and protects the wearer's medical data, which can then be downloaded to a computing device whenever someone is incapacitated or goes to a hospital, to a new doctor, etc. This item is a secure device such that if/when it is damaged or tampered with, it wipes all internal data thereby accommodating HIPAA regulations. The device communicates with a server to authenticate and send back medical data in a usable format for the hospital/doctor, wirelessly in one embodiment. The medical data at the user's option is stored on the device, on the server, or both. The device communicates with the server over an Internet connection, such as the Internet connection of a connected computing device or a wireless network (if the device has wireless capability), or a cell signal. A password connects the user to the secure device so that if lost or stolen, the data contained therein remains inaccessible. Emergency accessibility exists for conditions like incapacitation or identifying a body, for police/emergency responders, etc.

A new system includes a portable device having a person's personal medical information stored on a non-transitory computer readable medium, an activation mechanism, and a computing device communication mechanism such as a USB connector, serial, firewire, or other connector, wireless transceiver, etc. The system also includes a remote authenticating computing device (e.g. server, which may be a computer or smart phone or other device) connected to a computing device network and having authentication information stored on a non-transitory computer readable medium, an authentication software module and a diagnostic software module.

The activation mechanism, when operated by a user, causes the PMDST to initiate communications, via the built-in communication mechanism (such as a USB connector, serial, firewire, or other connector, wireless transceiver, etc.) with the remote authenticating computing device over a computing device network. The activation mechanism in some embodiments is a button, switch, or other mechanical feature on the PMDST casing, and in other embodiments is implemented in software or hardware internally and is activated automatically or through a user interface when the PMDST is physically or wirelessly connected to a computing device. The activation mechanism is particularly useful in embodiments with wireless connections, where the PMDST may come within range of computing device s and networks when a connection is not desired.

The portable PMDST device does not allow the medical information to be accessed without authentication. The authentication software module requests authentication information from a user, for example through a computing device using a web interface, receives authentication information input by the user, verifies received authentication data against the authentication information stored on the non-transitory computer readable medium, and after successful verification allows the medical information to be accessed by a computing device. The diagnostic software module determines whether the portable device has been damaged or tampered with and the stored medical information is destroyed when it determines that there has been damage or tampering.

In a new method, a portable PMDST device having a non-transitory computer-readable medium storing medical information is connected with a computing device which, in an embodiment, is a local computing device; a remote authenticating computing device is communicated with; authorization information is entered through the local computing device; and the medical information is retrieved from the portable device using the local computing device.

In a new method, a remote authenticating computing device connected to a computing device network and comprising authentication information stored on a non-transitory computer readable medium is provided, the remote authenticating computing device is communicated with a portable device storing a person's personal medical information over a computing device network, authentication information is requested from a user, authentication information input by the user is received, received authentication data is verified against the authentication information stored on the non-transitory computer readable medium, after successful verification, a signal is sent allowing the medical information on the portable device to be accessed by a computing device, whether the portable device has been damaged or tampered with is determined and the medical information is destroyed when there has been damage or tampering.

In one embodiment, identification authentication information is provided to emergency responders, the identification authentication information is unique to each emergency responder, the identification authentication information is received, and an authorization key is transmitted.

A new device includes a portable casing supporting a non-transitory computer readable medium storing medical information, an activation mechanism, and a computing device communication mechanism. The activation mechanism, when operated by a user, causes the device to communicate with a remote authenticating computing device over a computing device network. The portable device does not allow the medical information to be accessed without authentication. The medical information is destroyed when tampering or damage to the device is detected. The portable device allows the medical information to be accessed when it receives confirmation of authentication through the computing device communication mechanism.

A new system includes a remote authenticating computing device connected to a computing device network and having authentication information stored on a non-transitory computer readable medium, an authentication software module and a diagnostic software module. The authentication software module requests authentication information from a user, receives authentication information input by the user, verifies received authentication data against the authentication information stored on the non-transitory computer readable medium, and transmits authentication confirmation information to a portable device storing medical information. The diagnostic software module determines whether the portable device has been damaged or tampered with and the stored medical information is destroyed when it determines that there has been damage or tampering.

In one embodiment a user interface resides on a server and the server loads this user interface on the local computing device when communicated with, allowing the authorization information to be entered through the interface. The ibutton holds an application that reports out the data in a template format and can convert to pdf, txt, doc formats, etc.

These and further and other objects and features of the invention are apparent in the disclosure, which includes the above and ongoing written specification, with the drawings.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein.

DETAILED DESCRIPTION

Figure 1:
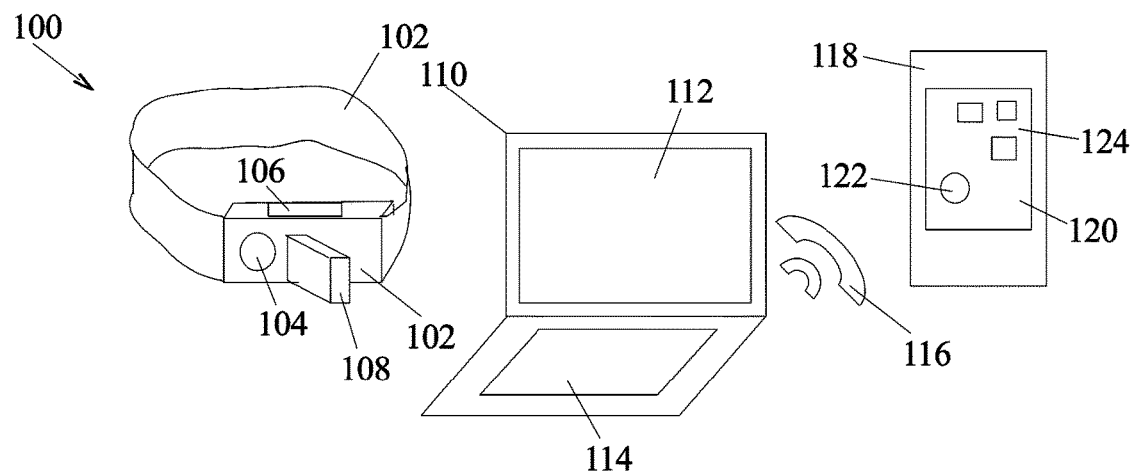
FIG. 1 is a diagram of a medical alert tamper-proof secure device system.

A medical alert computer interface tamper-proof secure device will now be disclosed in terms of various exemplary embodiments. This specification discloses one or more embodiments that incorporate features of the invention. The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may effect such feature, structure, or characteristic in connection with other embodiments whether or not explicitly described.

In the several figures, like reference numerals may be used for like elements having like functions even in different drawings. The embodiments described, and their detailed construction and elements, are merely provided to assist in a comprehensive understanding of the invention. Thus, it is apparent that the present invention can be carried out in a variety of ways, and does not require any of the specific features described herein. Also, well-known functions or constructions are not described in detail since they would obscure the invention with unnecessary detail.

FIG. 1 is a diagram of a medical alert tamper-proof secure device system 100. Medical alert bracelet 102 has a casing 102 containing an ibutton 104, storage device 106, and USB connector 108. To access the wearer's medical history, the bracelet is connected to a computer 110 with the USB connector 108, which communicated 116 with authorization server 118. An authorization request from the authorization server 118 is displayed on the computer's display 110 and a user can input authorization information using the computer's input device 114. The authorization server contains a computer readable medium 120 which contains various software modules 124 and databases 122 for carrying out authorization.

Figure 2:
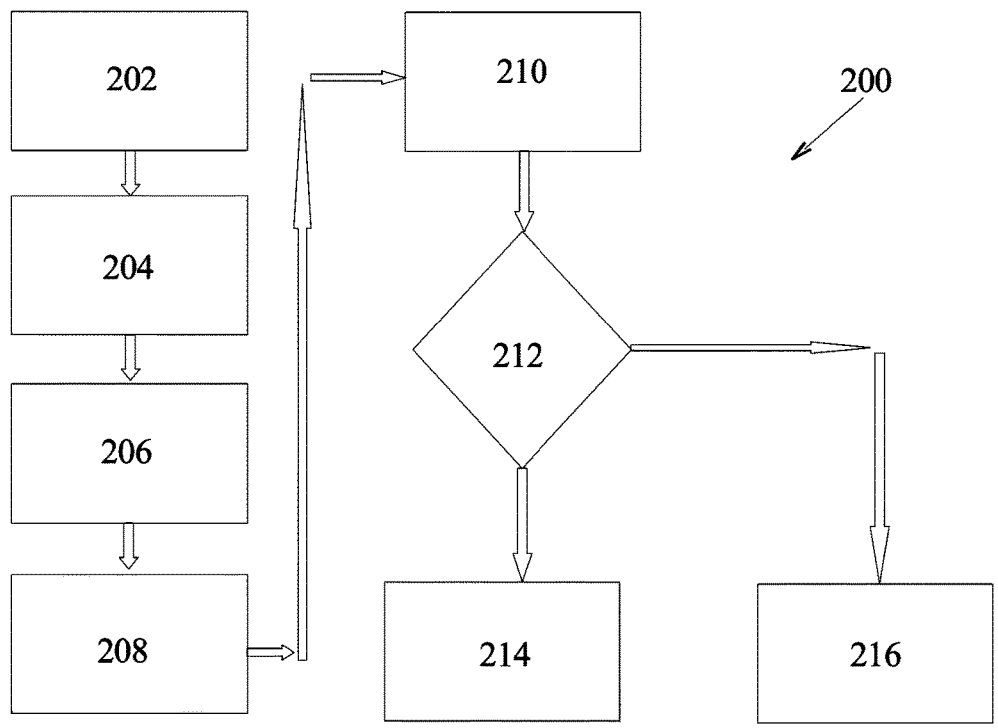
FIG. 2 is a flowchart of an authorization process.

FIG. 2 is a flowchart of an authorization process. The medical alert device is connected 202 to a local computer. Via the local computer, a unique ID is communicated 204 to the remote authorization server. The remote authorization server identifies 206 the device based on the unique ID, and requests 208 that a password or key be entered on the user end, at the local computer. The password is entered 210 into the local computer, and conveyed to the authentication server. The authorization server verifies 212 that the password/key sent from the user matches one stored on the authentication server and associated with the particular device. If so, the authorization server authorizes 214 the local release of data from the device and/or from the server. Otherwise, the authorization server does not authorize access to the device and repeats its request for password/key 216.

A new personal medical alert device (already referred to above as a Patient Medical Data Storage Tag, or PMDST for short) contains a user's medical history and requires authentication to access this medical history. In one specific embodiment, the device is worn by the user e.g. as a bracelet or other piece of jewelry and emergency care providers are given authentication information in advance or by a third party for use when the user is incapacitated. In another embodiment, the PMDST may be a plastic card, similar to a credit card or to the plastic Medic Alert cards already issued by the Medic Alert foundation, but with additional elements coupled to it is such as memory, activation mechanism, ibutton, and/or other elements as described herein.

In certain embodiments, the medical history is destroyed if the PMDST device is damaged or tampered with; the device stores the medical history on a USB flash memory or similar memory; the device has an ibutton that contacts a server, checks the state of the device, and requests a password and key; the medical history can be accessed in web format or downloaded; updated medical history can be entered in the web format or uploaded to the device; the medical history is stored on a server for web access; the USB uses encryption (including for example and without limitation 128 or 256 bit hex key encryption-the encryption is in some embodiments created elsewhere than the USB device, such as on an authorization server in order to unlock the device); and the device uses a wireless interface and waterproof case. In an alternative embodiment, if the PMDST device is damaged or tampered with, the medical history is not destroyed, but may be subject to immediate additional encryption or additional layers of password protection, which can only be removed or decoded by selected, specialized personnel.

In one embodiment, emergency responders are given a unique URL address in advance that they can use to generate a one-time-use key for the PMDST as needed. The unique URL is to verify the identity of the emergency responders and in some embodiments is given out based on tax ID or another identifying feature. In one embodiment, the PMDST device is connected to a computing device and either the patient or a doctor or other emergency medical response user navigates to a secure website and logs into an account, generates a key from the website, and inputs the key into the website, and the website unlocks the device for one use to access and update the medical history.

In an exemplary embodiment, the authentication process works as follows. The medic alert device contains an ibutton with a factory-set unique ID identifying the particular medic alert device. The ibutton has an application to run data destruction, detect fraud attempts, etc. The device is hooked up to a local computer (via cable or wireless network, or similar). Via the local computer, the unique ID is communicated to a remote authentication server. The remote authentication server identifies the device based on the unique ID, and finds a password or similar associated with the unique ID. A temporary password for an emergency responder may be associated with the unique ID. For example, if an emergency responder has been dispatched to an emergency scene, and a temporary password is created to match the unique ID for that one emergency occasion.

The remote authentication server requests that a password or key be entered on the user end, at the local computer. The password is entered into the local computer, and conveyed to the authentication server. In other embodiments, the user enters a software key of some kind The password is alphanumeric in some embodiments, but in other embodiments is biometric, audible, or otherwise non-alphanumeric. In the event that the password/key sent from the user matches that stored on the authentication server (and associated with the particular device), the authorization server authorizes the local release of data from the device and/or from the server. In some embodiments the authorization can authorize full or partial access to the device through the local computer, depending for example on user preferences, state laws, or the password entered (an emergency responder may have different rights than the user for example).

In some embodiments a PMDST is a self-contained, portable, secure medical alert device which is carried/worn by a patient and is capable of containing, updating and downloading an individual's entire medical history. In some embodiments, while data updating and amending are allowed, data deletion is not, preventing a patient from altering data a doctor inputs, or data a pharmacist inputs in order to hide drug use. The PMDST is authenticated by using passwords and keys (public and private) to unlock the history. Each file in one embodiment has two sets of keys for server verification/security. The public key is for example made up of the date of the ibutton and a serial number, the private key is created on the server.

If the PMDST is damaged or tampered with, the files destruct or additional data encoding or protection is added on the fly. iButtons run applications that can detect any unauthorized attempts to access data and if connected to the usb drive, they can restrict any ability to access data on the USB.

Data can only be accessed using passwords on a secure sever to unlock data. The device information is made available to emergency care providers such as hospitals, police, EMT's, etc. They are given specific keys which unlock the device information when an individual is incapacitated and cannot provide guidance for treatment.

In some embodiments the device is packaged inside of a fashionable piece of men's/ladies jewelry made of stainless steel. The caduceus is incorporated in the design so that EMT's know this is a med alert device.

In some embodiments the PMDST device includes a small USB device and ibutton for security. For example, at current levels of technology, a small device may have 8 Gbytes of memory. However, with advances in story capacity, other amounts of memory may be envisioned over time. The ibutton contacts a server, checks the state of the device (working/not tampered with, etc.) and requests a password and key. The server checks the state of the device each time it is contacted, but the ibutton also monitors the state of the device. The ibutton holds a software application that contacts the secure server and pushes data from the device to the server. The server requests the password and the ibutton holds the keys. Once authentication takes place (the server has unlocked the device), the data is available for use in a web format and may be downloaded to a computing device in a variety of formats. The ibutton also holds a conversion application that allows the data stored on the device to be downloaded directly to a computing device. This is useful in case a physician/hospital needs to download the data and the owner has not chosen to have it held on a server.

In one exemplary embodiment, the PMDST device is connected to a local personal computer (PC), and the PMDST device calls a URL on the Internet through the PC. The website user interface opens a password dialog box to unlock the device (the password held in the ibutton), then requests another password to unlock the site database for updating/viewing.

The data may be updated in the web format or uploaded using a variety of formats to the device. The user can directly input data through the web interface should they elect this feature, or a physician can update the data based on what features are selected by the owner. In some embodiments, a physician or pharmacist can input data without the device being present. Allowing this convenient access by medical professionals provides a secure check that therapies are properly being carried out, prevent phama errors in filling scrips, and provide a check on drug over use. In some embodiments, third parties such as an insurance company are given authorization to access certain data in case of malpractice or legal action on accidents, etc. A conversion application allows download to a PC or the device in a variety of data formats so that there is flexibility for the user and/or caretakers. Should the password be forgotten there is a toll-free number and security questions to answer to retrieve the password, in which case the password is sent by email (or text message, etc.) or the device is manually unlocked by the server.

As a value-added service, an individual may request that his or her medical history be stored on a server, in addition or instead of the device, for a small annual fee. This can be retrieved in a web format and updated/downloaded by hospitals/physicians. Digital x-rays, MRI's, ultrasounds, CAT scans, etc. may be stored here, although even a modest 8 GB USB storage device is large enough to store a lifetime of medical data including x-rays, MRI results, CAT scans, etc. This backup storage will allow a user to restore their data if an attempted tampering destroys the data stored on the user's portable device.

In one embodiment, a user purchases a med alert device and gets the hardware device and a web account that is on a secure server. The device is a USB with, for example, 128 bit or 256 bit hex key encryption created on a server to unlock the device and a tamper-proof application running inside of a med alert bracelet that can unlock the device using the key. A new one-time-use key is created each time the device is connected. This encryption method, used in place of an ibutton, reduces the amount of memory necessary in the portable hardware.

When the device is connected to a computing device, a remote authorization server is called and the user is prompted for login credentials (e.g., password and/or username). After a successful login, the authorization server creates a one-time key that is transmitted to the user. The user then enters this key into the device to unlock it. In some embodiments, the login information is entered into a website interface and the key is entered into an interface generated by the tamper-proof application or a website interface.

The device is connected to a computing device, the user navigates to a secure website, logs into an account using a password, generates a key from the website, puts the key into the website, and the website unlocks the device for this one use. Then doctors, hospitals, etc. can update the account and download to the device. It is an easy matter for police and emergency personnel to access the data with a phone call and emergency key to unlock the device. The emergency key in one embodiment is generated upon verification of emergency personnel's tax ID.

In some embodiment, the device includes a wireless interface and waterproof case, making it resistant to the elements and eliminating the need for a USB connection. In some embodiments, the user interface resides on the server and is transmitted to the computing device over a network such as the Internet, and may be accessed and displayed via a web browser or directly, in various embodiments.

The device has many advantages over the prior art. Currently when patients go to a physician, they need to fill out forms with medical history data, these are left to the winds of memory of the patient. This device has a complete medical history that can be updated, hold digital MRI, CAT scan and x-ray results, allergy information, identification, phone and address information, etc. The device in some embodiments stores complete medical histories, including test results and other details that would be extremely difficult or impossible to carry around or remember, including the results of CT scans, EKGs, ECGs, stress tests, blood tests, bone density scans, spinal taps, urine tests, and other fluid analysis, eye tests, dental information, fMRIs, and genetic tests and analysis, as well as doctors' notes and other related documents. Being able to download a history or update a history with a download makes a physician's office more efficient and cuts down on data input and errors.

Prior art med alert bracelet and necklaces hold only allergy information. The memory device of this application is accessible to emergency workers when the patient is unconscious or unresponsive, holding all of the medication information for doctors treating these patients. This helps avoid medical slip-ups with competing medications or allergic reactions to medication. Also, this provides a written history which is not subject to a patient's memory. If the individual has died and carries the device, they can be identified more easily by matching physical characteristics with the medical data.

This device is valuable to any and all individuals in developed countries with well developed IT networks. It allows an individual to carry his or her medical history for easy access in case of emergency or to update physician records. The device is designed especially for retail consumers, particularly those who have allergies or who just want an easy upload at the physician's instead of filling out forms. Older citizens who just cannot remember all of their medical history will find the device particularly advantageous. The device reduces medical errors and improves office efficiencies.

In one embodiment, the device is a stainless steel, fashionable medical alert bracelet which contains a USB device connected to an iButton, in which case the iButton handles the encryption, or which uses 128 Bit encryption, in which case a piece of hardware runs the encryption program, which interfaces with a computing device. Custom software and mechanical hook ups with the server interface are used to complete the device functionality and a case designed to look like a fashionable piece of jewelry is also used in some embodiments, which can be achieved at low cost to produce an attractive end product for consumers.

In order to help support the current federal administration's push to move medical practitioners to digital formats, an additional service/business case is offered. Small medical offices may connect to the master network and receive the digital services including office management and file management (a variety of programs are offered, licenses specific to the practice may be purchased by the practitioner's office).

Small medical offices run their office from the servers, using whatever service features they elect, e.g. data storage, payroll, calendaring, purchasing/inventory maintenance, etc. They purchase the hardware and a license to run the software features. They would not need servers or server maintenance or need to worry about updates. This system reduces the costs to meet the government's initiative to become "digital" compared to the cost to a physician to install or upgrade their equipment to bring their office online, around $40K on average. The server farm (overhead that is in existence) maintains the data—this obviates the need for hardware, maintenance and investment for the doctors and offers an income stream for the operator. Volume discounts on purchases of hardware could also be accessed by physicians.

Practitioners who maintain patient data in digital form on the server are able to analyze and verify this data automatically, allowing them to check for example for abuse of prescription medications. This abuse could be stopped by checks and balances with the data, for example automatically analyzing the data for signs of excessive painkiller use, reducing healthcare costs.

In one embodiment, the device is used for another application. Municipal parking meters interact with an ibutton which gives the meter a unique-secure address to process cash transactions, and accounts on the servers backed by a credit card. The credit card owner can communicate with the servers through phone or internet and refill the "universal" (nationwide/worldwide) account. The ibutton then communicates with the server and credits the state/municipality with the parking cost from the universal account. The meter can signal low credit and request a refill using the ibutton, then an amount can be punched in.

The ibutton is part of the meter and used as a secure device in order to allow the meter to securely download money to smart cards. Example: a user puts a smart card in the meter, the meter checks the amount left on the account and determines that there is not enough money. The meter asks if the user wants to add money, if the user responds yes it contacts the server, asks the user how much he or she wants to add, the user inputs the amount, and the smart card is updated correspondingly. Thus, a parking ticket resulting from insufficient funds is avoided. The owner can contact the universal account in a variety of ways, but the money has to be updated to the smart card via the meter using the secure ibutton application. Smart cards or similar payment devices are used as alternatives to credit card payments for increased convenience and security. The use of at-meter ibutton authenticated reloads further increases the convenience and security.

Figure 3:
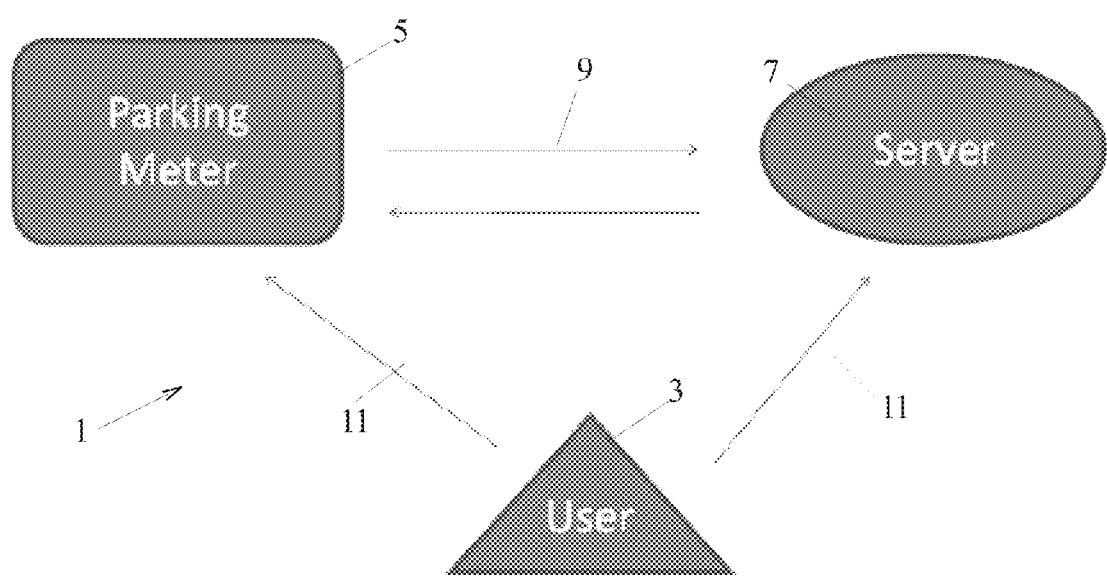
FIG. 3 is a diagram of a municipal parking meter payment system.

FIG. 3 is a diagram of such a municipal parking meter payment system 1. A user 3 communicates 11 with a server 7 to refill its universal account and communicates 11 with the parking meter 5 to make payment for parking and/or update the value of a parking smart card. Parking meter 5 and sever 7 share a two-way communications link 9, through which the parking meter can communicate its identifying information and transaction details and the server can communicate payment information, permitting the parking meter 5 to update the value of the user's smart card from the universal account.

The invention is not limited to the particular embodiments illustrated in the drawings and described above in detail. Those skilled in the art will recognize that other arrangements could be devised, for example, using various encryption and authentication methods and device casings and shapes. The invention encompasses every possible combination of the various features of each embodiment disclosed. While the invention has been described with reference to specific illustrative embodiments, modifications and variations of the invention may be constructed without departing from the scope of the invention.

I claim:

1. A system, comprising:
   a portable mechanical element configured for transport on a person's body;
   a non-transitory computer readable medium physically coupled to the mechanical element and configured to store:
   a person's medical information; and
   authentication data;
   a communications module coupled to the mechanical element and configured to communicate over a computer network with a validating computing device; and
   an authorization server configured to receive the authentication data of the portable mechanical element, determine a first authentication code associated with the mechanical element, request from a person having access to the electronic device a second authentication code, determine that the second authentication code matches the first authentication code, and based on the match of the first authentication code with the second authentication code, issue an authorization for the electronic device to release confidential patient medical data,
   wherein the computer readable medium is configured to allow access to the person's stored medical information only if the authorization is issued.

2. The system of claim 1, wherein the portable mechanical element or the authorization server further comprises a diagnostic module configured to determine whether the portable device has been damaged or tampered with, and further configured to prevent access to the stored medical information upon a determination of damage or tampering.

3. The system of claim 2, wherein the diagnostic module is configured to prevent access to the stored medical information by destroying the stored medical information.

4. The system of claim 1, wherein the portable mechanical element further comprises an activating element configured to initiate access to the person's stored medical information.

5. The system of claim 1, wherein the computer readable medium is further configured to allow access to the person's stored medical information only upon receiving from the validating computer device a validation of at least one of:
   the owner of the portable device; and
   emergency personnel authorized to have access to the data on the portable mechanical element.

6. The system of claim 1, further comprising an indicia designating the mechanical element as being provisioned for the conveyance of personal medical information.

7. The system of claim 1, wherein the mechanical element further comprises a casing in the shape of a piece of a bracelet or other piece of jewelry.

8. The system of claim 1, wherein the portable device further comprises a waterproof casing.

9. The system of claim 1, wherein the computer readable medium is configured to allow access to the person's stored medical information for viewing or modification, but not for downloading.

10. The system of claim 1, wherein medical information is also stored on the remote authorization server or another remote device connected to a computing device network and is accessible to the user over the computing device network with or without the portable device.

11. The system of claim 1, wherein the authorization server further comprises stored unique URL addresses and is configured to transmit an authentication code to a user navigating to a stored unique URL address.

12. A method, comprising:
   connecting with a computing device a portable mechanical element configured for carrying on an individual patient and comprising a non-transitory computer-readable medium configured to store medical information pertaining to the individual patient, establishing a communication between the computing device and a remote authenticating device, conveying via the computing device from the portable device to the remote authenticating device an identification of the portable device, entering through the computing device authorization information for access to the medical information pertaining to the individual patient, receiving from the remote authenticating device a confirmation of a match between an authorization information stored on the remote authenticating device and the entered authorization information, and retrieving a stored medical information pertaining to the individual patient from the portable device.

13. The method of claim 12, wherein the portable mechanical element comprises an activation mechanism, wherein establishing a communication comprises manipulating the activation mechanism.

14. The method of claim 12, wherein the entering through the computing device authorization information comprises loading a secure website using the computing device, logging into an account, generating a key from the website, and entering the key into the website.

15. The method of claim 12, wherein the entering through the computing device authorization information consists of entering a pre-existing key unique to an emergency responder.

16. The method of claim 12, wherein the entering through the computing device authorization information consists of entering a pre-existing key unique to an emergency responder and verifying an emergency responder identity.

17. A method for controlling release of patient medical data, comprising:

receiving, at an authorization server, an identification of an electronic device containing confidential patient medical information;

determining at the authorization server a first authentication code associated with the electronic device;

requesting from a person having access to the electronic device a second authentication code;

determining at the authorization server that the second authentication code matches the first authentication code;

based on the match of the first authentication code with the second authentication code, issuing from the authorization server an authorization for the electronic device to release confidential patient medical data.

18. The method of claim 17, further comprising:

receiving at the authorization server a status data from the electronic device;

determining at the authorization server based on the status data if the electronic device has been modified, damaged, or tampered with; and upon the determination, issuing from the authorization server to the electronic device a command which blocks the release of the confidential patient medical data from the electronic device.

19. The method of claim 17, further comprising storing the medical information and transmitting some or all of the medical information based on the match of the first authentication code with the second authentication code.

20. The method of claim 17, further comprising providing identification authentication information to emergency responders, wherein the identification authentication information is unique to each emergency responder, receiving the identification authentication information, and transmitting an authorization key.

21. A device, comprising:

a portable mechanical element configured for transport on a person's body;

a non-transitory computer readable medium coupled to the mechanical element and configured to store:

a person's medical information; and authentication data; and a communications module configured to communicate over a computer network with a validating computing device;

wherein the computer readable medium is configured to allow access to the person's stored medical information only if the authentication data stored on the portable device is validated by the validating computer device and only upon receiving from the validating computing device a validation of the user of the portable device.

22. The portable device of claim 21, further comprising at least one of:

a diagnostic module configured to determine whether the portable device has been damaged or tampered with, and further configured to prevent access to the stored medical information upon a determination of damage or tampering; and means for coupling to a remote diagnostic module configured to determine whether the portable device has been damaged or tampered with, and further configured to prevent access to the stored medical information upon a determination of damage or tampering.

23. The portable device of claim 22, wherein the diagnostic module is configured to prevent access to the stored medical information by destroying the stored medical information.

24. The portable device of claim 21, further comprising an activating element configured to initiate access to the person's stored medical information.

25. The portable device of claim 21, wherein the computer readable medium is further configured to allow access to the person's stored medical information only upon receiving from the validating computer device a validation of at least one of:

the owner of the portable device; and a medical professional authorized to have access to the data on the portable device.

26. The portable device of claim 21, further comprising an indicia designating the mechanical element as being provisioned for the conveyance of personal medical information.

27. A system, comprising:

an authorization server configured to receive an identification of an electronic device containing confidential patient medical information, determine a first authentication code associated with the electronic device, request from a person having access to the electronic device a second authentication code, determining that the second authentication code matches the first authentication code, and based on the match of the first authentication code with the second authentication code, issue an authorization for the electronic device to release confidential patient medical data.

28. The system of claim 22, wherein the authorization server is configured by a software module stored on a non-transitory computer readable medium.

29. The system of claim 22, wherein the authorization server is further configured to receive a status data from the electronic device, determine based on the status data if the electronic device has been modified, damaged, or tampered with, and upon the determination, issue to the electronic device a command which blocks the release of the confidential patient medical data from the electronic device.

\* \* \* \* \*